United States Patent [19]

Hearon et al.

[11] 4,073,804
[45] Feb. 14, 1978

[54] PRODUCING GLYCINE BY THE REDUCTIVE AMINATION OF GLYOXYLIC ACID

[75] Inventors: William Montgomery Hearon, Portland, Oreg.; Lo Cheng Fan, Vancouver, Wash.

[73] Assignee: Boise Cascade Corporation, Portland, Oreg.

[21] Appl. No.: 682,831

[22] Filed: May 4, 1976

[51] Int. Cl.$^2$ .................... C07C 99/00; C07C 101/06
[52] U.S. Cl. ................................................ 260/534 R
[58] Field of Search ..................................... 260/534 R

[56] References Cited

U.S. PATENT DOCUMENTS

| | | | |
|---|---|---|---|
| 2,542,812 | 2/1951 | Hartung | 260/534 X |
| 3,354,203 | 11/1967 | Little | 260/534 R |
| 3,356,698 | 12/1967 | Lafont et al. | 260/534 X |

OTHER PUBLICATIONS

Greenstein et al., Chem. of the Amino Acids, vol. 1, John Wiley & Sons, Inc. N. Y. pp. 702–703, 713, (1961).
Kaneko et al., Synth. Prod. Util. of Amino Acids, John Wiley & Sons, N. Y. pp. 113–116, (1974).
Desnuelle et al., Bull. Soc. Chim, 5, 1, pp. 700–702.
Schoenheimer et al., J. Biol. Chem., 127, pp. 301–313, (1939).

*Primary Examiner*—James O. Thomas, Jr.
*Assistant Examiner*—G. T. Breitenstein
*Attorney, Agent, or Firm*—Eugene D. Farley

[57] ABSTRACT

Glycine is produced by the reductive amination of glyoxylic acid in a reaction mixture comprising glyoxylic acid, ammonia, water and a water-soluble organic solvent for glyoxylic acid, in an atmosphere of hydrogen, using a rhodium hydrogenation catalyst.

9 Claims, No Drawings

PRODUCING GLYCINE BY THE REDUCTIVE AMINATION OF GLYOXYLIC ACID

BACKGROUND AND SUMMARY OF THE INVENTION

This invention relates to the production of glycine by the reductive amination of glyoxylic acid according to the following reaction:

$$OHC \cdot COOH + NH_3 + H_2 \rightarrow NH_2CH_2COOH + H_2O$$

Glycine (glycocoll; aminoacetic acid) is an industrial chemical having important and varied uses. Because of its amphoteric nature, it is used widely as a buffering agent, particularly in pharmaceutical and cosmetic preparations. It also has extensive application as a food-grade antioxidant, as a corrosion inhibitor, in electroplating, as an additive to saccharin for preventing its bitter after taste, and in the manufacture of plastics and polymers.

At the present time glycine is manufactured commercially from ammonia and glycolonitrile by a procedure outlined in U.S. Pat. No. 3,813,434. However, this method is complex; involves the use of a toxic reagent (HCN); and leads to the production of glycine in a reaction mixture from which it is isolated in the pure condition only with difficulty.

It has been proposed to produce glycine directly from glyoxylic acid by the reductive amination of the latter in aqueous solution using a palladium catalyst (Desnuelle et al. Bull. Soc. Chim [5] 1, 700-2 (1934); Chemical Abstracts Volume 28 column 6,700 1934). The proposed procedure has the additional advantage of employing as a starting material glyoxylic acid, which is readily available at low cost on the large commercial scale as a product of the controlled, oxidative degradation of cellulose, and especially of paper-making pulps and sludges. (Hearon et al. U.S. patent application Ser. No. 628,888, filed Nov. 5, 1975, now U.S. Pat. No. 3,998,878, for SELECTIVELY SEPARATING OXALIC, TARTARIC, GLYOXYLIC AND ERYTHRONIC ACIDS FROM AQUEOUS SOLUTIONS CONTAINING THE SAME.)

However, the procedure for the reductive amination of glyoxylic acid reported by Desnuelle et al. supra, indicates little promise for the successful commercial application of the procedure, since the glycine product is obtained in a yield of only 8% of the theoretical, and can be isolated from the complex reaction mixture only in the form of a derivative, i.e., the beta-naphthylsulfonate.

The reason for the lack of success in executing the proposed synthetic procedure is evident when it is considered that numerous side reactions leading to the production of numerous byproducts can occur when it is attempted to produce glycine by treating glyoxylic acid with ammonia in an atmosphere of hydrogen and in the presence of a hydrogenation catalyst. Among these are:

The reduction of glyoxylic acid to glycolic acid.

The dimerization and trimerization of glyoxylic acid.

The autooxidation and reduction of the glyoxylic acid in alkaline medium by the well known Cannizzaro reaction to produce oxalic acid and glycolic acid.

The reaction of any of the foregoing acids with ammonia to form ammonium salts of varying degrees of solubility in the reaction medium.

We now have discovered, and it is the essence of the present invention, that the foregoing problems may be overcome and glycine produced directly from glyoxylic acid in yields of up to about 97% by weight by reductive amination carried out with a colloidal rhodium catalyst in a reaction medium comprising a mixture of water and selected water-soluble solvents employed in amounts predetermined to maintain the reactants and reaction products in solution, and to inhibit the occurrence of undesirable side reactions, in particular the Cannizzaro reaction.

In its broad aspect, the hereindescribed process comprises forming a mixture of glyoxylic acid, ammonia and water together with a selected water-soluble organic solvent used in amount sufficient to insure the solubility of the intermediate reaction products during the progress of the reaction and the separation of the desired glycine product at its conclusion.

The reaction mixture is subjected to the action of gaseous hydrogen in the presence of a colloidal rhodium hydrogenation catalyst at pressures ranging from substantially atmospheric pressure to pressures of the order of 3,000 pounds per square inch, and at temperatures varying from just above the freezing point of the reaction mixture to 40° C. The reaction is permitted to proceed until the theoretical amount of hydrogen has been absorbed by the system, which occurs usually in from 1 to 16 hours. At the conclusion of the reaction, the catalyst is removed by filtration, the filtrate concentrated, and a suitable precipitating solvent such as methanol added. Thereupon the glycine separates as a white precipitate which may be separated from the mother liquor by filtration.

DESCRIPTION OF PREFERRED EMBODIMENTS OF THE INVENTION

The starting material for the hereindescribed process for the production of glycine comprises glyoxylic acid (OHCCOOH) which, as is well known, under some conditions exists as the hydrate, dihydroxy acetic acid $(HO)_2CHCOOH$. Either of these materials is suitable as a starting material for the present process and each is comprehended herein under the term "glyoxylic acid." As noted above, this compound is potentially available in very large quantities and at low cost as a product of the oxidative conversion of cellulosic pulps to various products including glyoxylic acid.

In carrying out the reductive amination, the glyoxylic acid is placed in an aqueous mixture containing in addition to itself ammonia, water, and a water-soluble organic solvent for the glyoxylic acid.

The ammonia may be employed either as aqueous ammonia or as liquid ammonia. In view of its capacity for forming salts with both the glyoxylic acid starting material and the glycine product, it is employed in an amount equal to at least 2 mols of ammonia for each mol of glyoxylic acid. Preferably from 2-4 mols of ammonia are added for each mol of glyoxylic acid which thereby is converted to various known intermediate reaction products of glyoxylic acid and ammonia.

A variety of water-soluble organic solvents may be used in conjunction with the water in order to achieve the purpose of maintaining the reactants, the intermediate products and the glycine end product all in solution during the course of the reaction. Such solvents additionally should be nonreactive toward the glyoxylic acid and the glycine, low boiling, of reasonable cost, and recoverable and recycleable at the conclusion of the reaction.

Solvents fulfilling the foregoing criteria comprise 1,4-dioxane, tetrahydrofuran, piperidine, and the water miscible lower aliphatic alcohols, i.e., methanol, ethanol, the propanols and tertiary butanol. Of these, methanol is a preferred solvent because of its availability, low cost, and efficient action.

As noted, the ratio of water-soluble organic solvent to water is predetermined to keep the reactants and reaction products in solution and promote the conversion of the glyoxylic acid to glycine. When methanol is used as the organic solvent, a solvent mixture comprising about 60% methanol and 40% water gives satisfactory results. More broadly stated, from about 40 to about 70% by weight methanol preferably is employed with reference to the total weight of the methanol-water solvent mixture.

Also included in the reaction mixture is a suitable hydrogenation catalyst. We have discovered that of the usual group of such catalysts, including ruthenium, rhodium, nickel, palladium, platinum and osmium, only rhodium is effective in producing high yields of glycine.

The catalyst is used in catalytic amount in the form of particles of the elemental material. As is usual, it preferably is employed in a finely divided (colloidal) form deposited on a suitable carrier such as alumina or carbon.

The reactants are placed in a pressure vessel equipped or associated with means for vigorous stirring and agitation as well as for the introduction of hydrogen gas under conditions predetermined to maintain the desired pressure within the reactor. Depending upon the catalyst employed and the other conditions of the reaction, pressures from atmospheric pressure to 2,000 or 3,000 pounds per square inch may be employed. In the usual case, a pressure of from about 20 to about 60 pounds per square inch is adequate.

The reaction does not demand high temperatures. Broadly, temperatures of from just above the freezing temperature of the mixture to about 40° C., preferably from about 15° to about 30° C., are optimum. More elevated temperatures favor the production of undesired by-products of the character discussed above.

The reaction is carried on to completion, usually as noted by the failure of the system to absorb a further quantity of hydrogen. This time is somewhat variable depending upon the other conditions of reaction. In general, however, a reaction period of from 1 to 16 hours suffices to complete the reaction. Longer reaction periods may be employed where desired, as in order to adapt the reaction to plant operating schedules.

The process of the invention is illustrated by the following examples.

EXAMPLE I

A 500 ml. pressure bottle containing 20 ml. methanol (practical grade) and 0.02 g. 5% rhodium on carbon was shaken with 30 psig hydrogen for 20 minutes. A 100 ml. graduated cylinder maintained at 20° C. with an ice bath was filled with 30 ml. methanol and then 10 ml. liquid ammonia, followed by adding 5 ml. 38.8% glyoxylic acid (2.506 g. of 100% glyoxylic acid), diluted with water to 25 ml. and added dropwise over a period of 10 minutes.

The resulting mixture then was poured into the pressure bottle containing the methanol-suspended catalyst.

The system was hydrogenated at 45 psi and 20° to 25° C. for 7.50 hours, i.e., to completion of reduction. The catalyst was removed by filtration. The filtrate after evaporation to 10 ml. under reduced pressure at 50° C. was precipitated by the addition of 90 ml. methanol. After standing for six hours the mixture was filtered and the resultant white solid (glycine) dried in an oven at 100° C. for 1.00 hours. It weighed 2.4567 g. (96.7% of theory). Its identity as glycine was established by its melting point of 232°–233° C., its mixed melting point of 232°–235° C, with known glycine, paper chromatography, and its sweet taste.

EXAMPLE II

This example illustrates the reductive amination of glyoxylic acid to glycine in various solvent systems.

Glyoxylic acid solution (2.00 g) derived from the oxidative degradation of cellulosic papermill pulp and containing 50.1% by weight glyoxylic acid; 0.100 g. of 5% rhodium on carbon catalyst, distilled water, ammonia and a selected water soluble organic solvent were placed in a 500 ml. Parr bottle and hydrogenated at 25 to 40 psig at room temperature (18°–22° C) until the theoretical amount of hydrogen was absorbed by the system.

At the end of the hydrogenation, the catalyst was removed by filtration and the light yellow filtrate was concentrated to about 10 ml. under reduced pressure at 45°–50° C. The resulting thick concentrate then was mixed with 90 ml. methanol and stirred for five minutes. After standing for 16 hours (over night) the glycine product was collected as a white precipitate on a filter and oven dried at 100° C. to constant weight. In each case the glycine product had a melting point of 229°–233° C. and a mixed melting point with a known sample of glycine of 230°–233° C. The composition of the solvent system employed, the reaction conditions and the results from each run are summarized in Table 1 below.

TABLE 1

| Type of Organic Solvent | System of the Solvent (ml) | | | | Hydrogenation Time (Hours) | Glycine | Yield % |
|---|---|---|---|---|---|---|---|
| | $H_2O$ | Organic Solvent | $NH_3$ | Type of $NH_3$ | | | |
| Dioxane | 20 (ml) | 45 (ml) | 2.00 (ml) | Liquid $NH_3$ | 7.50 | 0.7066 | 69.6 |
| Tetrahydrofurane | 10 | 50 | 25.00 | 28% aqueous solution | 7.50 | 0.8009 | 78.9 |
| Piperidine | 15 | 50 | 35.00 | 28% aqueous solution | 8.50 | 0.5967 | 58.8 |
| t-Butanol | 20 | 50 | 5.00 | Liquid $NH_3$ | 5.00 | 0.6483 | 63.8 |
| Methanol | 25 | 50 | 10.00 | Liquid $NH_3$ | 3.25 | 0.9740 | 95.9 |
| Ethanol | 15 | 60 | 20.00 | 28% aqueous solution | 16.00 | 0.9350 | 92.1 |

EXAMPLE III

This example illustrates the comparative inapplicability of platinum and palladium catalysts and hence the selective character of the hydrogenation catalyst employed in the reductive amination of glyoxylic acid to glycine by the hereindescribed process.

2.00 g. of 40.14% glyoxylic acid solution, 25 ml. water, 10 ml. 28% aqueous ammonia and 45 ml. ethanol were mixed at room temperature with 0.100 g. of the selected catalyst. The resulting mixture was placed in a 500 ml. Parr bottle and hydrogenated with agitation at 40 psig and room temperature until the theoretical amount of hydrogen was absorbed by the system.

The catalyst was filtered off and the light yellowish to white filtrate was concentrated to about 10 ml. under reduced pressure at 45°–50° C. The resulting thick concentrate then was mixed with 90 ml. methanol, stirred for 5 minutes and permitted to stand for 16 hours. The precipitated glycine product, if produced, was collected on a filter and oven dried to constant weight.

The conditions and results from each experiment are shown in Table 2 below.

TABLE 2

| Type of Catalyst | Completed Hydrogenation Time (Hours) | Glycine (g) | Yield (%) | Notes |
| --- | --- | --- | --- | --- |
| 5% Pt/Alumina | 30 | 0.3288 (White) | 40.4 | M.p. and mixed m.p. with glycine at 230–233° C. |
| 5% Pd/Alumina | <0.50 | 0.2100 | 25.8 | M.p. 203 – 4 mixed m.p. with glycine 206 – 209 Acid taste. |

EXAMPLE IV

This example illustrates the relatively low yield of glycine obtained using colloidal nickel as a catalyst.

Freshly prepared activated Raney Nickel 0.20 g; 50.14% by weight glyoxylic acid, 5.00 g; methanol 30 ml; water 40 ml; and liquid ammonia 4.00 ml. in a 500 ml. Parr bottle were shaken with 40 psig of hydrogen at room temperature for 17.00 hours. The total hydrogen absorbed by the mixture was 24.50 psig (theory = 24.17 psig).

The catalyst was filtered off and the light green filtrate was evaporated to about 5–10 ml. followed by mixing with 90 ml. methanol. After 6.00 hours, the precipitate (very light green color) was collected on a filter. The greenish color was not completely removed by washing with ammoniated methanol (ammonia:methanol) subsequently the precipitate was dried at 100° C to a constant weight of 0.8088 g (theory = 2.5408 g). The yield was 31.8% by weight.

The product had a sweet taste and a melting point and mixed melting point with glycine of 299°–230° C (theory = 234° C).

Having thus described our invention in preferred embodiments, we claim:

1. The process for the production of glycine which comprises:
   a. forming a solution of glyoxylic acid, ammonia, water and a water-soluble organic solvent,
      1. the ammonia being used in an amount of at least 2 mols of ammonia per mol of glyoxylic acid,
      2. the solvent being used in an amount sufficient to substantially dissolve the glyoxylic acid, ammonia and water; the intermediate reaction products of glyoxylic acid with ammonia; and the glycine product,
   b. hydrogenating the solution in an atmosphere of hydrogen in the presence of a metallic rhodium hydrogenation catalyst for a time sufficient to convert a substantial proportion of the glyoxylic acid to glycine, and
   c. separating the glycine product from the resulting reaction mixture.

2. The process for the production of glycine which comprises:
   a. forming a solution of glyoxylic acid, ammonia, water and at least one water-soluble organic solvent selected from the group consisting of 1,4-dioxane, tetrahydrofuran, piperidine, tertiary butanol, and the lower aliphatic alcohols having fewer than four carbon atoms,
      1. the ammonia being used in an amount of at least 2 mols of ammonia per mol of glyoxylic acid,
      2. the solvent being used in an amount sufficient to substantially dissolve the glyoxylic acid, ammonia and water; the intermediate reaction products of glyoxylic acid with ammonia; and the glycine product,
   b. hydrogenating the solution in the presence of a metallic rhodium hydrogenation catalyst at a temperature of from just above the freezing temperature of the reaction solution to about 40° C. and at a pressure of from about atmospheric pressure to about 3000 lbs. per square inch for a time sufficient to convert a substantial proportion of the glyoxylic acid to glycine, and
   c. separating the glycine product from the resulting reaction mixture.

3. The process of claim 2 wherein the organic solvent comprises methanol.

4. The process of claim 2 wherein the organic solvent comprises ethanol.

5. The process of claim 2 wherein the organic solvent comprises methanol used in an amount of from 40 to 70% by weight, based on the weight of the total methanol-water content of the reaction mixture.

6. The process of claim 2 wherein the hydrogenation of the mixture is effectuated at a pressure of from about 20 to about 60 pounds per square inch.

7. The process of claim 2 wherein the hydrogenation reaction is carried out at a temperature of from about 15° to about 30° C.

8. The process of claim 2 wherein the organic solvent comprises 40 to 70% by weight methanol, based on the weight of the total methanol-water content of the reaction solution, the hydrogenation catalyst comprises small particles of metallic rhodium, the hydrogenation pressure is from about atmospheric pressure to about 3,000 pounds per square inch and the hydrogenation temperature is from just above the freezing temperature of the reaction solution to about 40° C.

9. The process of claim 2 wherein the organic solvent comprises 40 to 70% by weight methanol, based on the weight of the total methanol-water content of the reaction solution, the hydrogenation catalyst comprises small particles of metallic rhodium, the hydrogenation pressure is from about 20 to about 60 pounds per square inch and the hydrogenation temperature is from about 15° to about 30° C.

* * * * *